(12) United States Patent
Liu

(10) Patent No.: US 10,465,229 B2
(45) Date of Patent: Nov. 5, 2019

(54) SYSTEM AND METHOD FOR DETECTING NEURAL INJURY

(71) Applicant: CASE WESTERN RESERVE UNIVERSITY, Cleveland, OH (US)

(72) Inventor: Chung-Chiun Liu, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/314,393

(22) PCT Filed: May 27, 2015

(86) PCT No.: PCT/US2015/032609
§ 371 (c)(1),
(2) Date: Nov. 28, 2016

(87) PCT Pub. No.: WO2015/183909
PCT Pub. Date: Dec. 3, 2015

(65) Prior Publication Data
US 2017/0101662 A1    Apr. 13, 2017

Related U.S. Application Data

(60) Provisional application No. 62/003,221, filed on May 27, 2014.

(51) Int. Cl.
*C12Q 1/32* (2006.01)
*G01N 27/327* (2006.01)
*G01N 27/30* (2006.01)

(52) U.S. Cl.
CPC ............. *C12Q 1/32* (2013.01); *G01N 27/301* (2013.01); *G01N 27/327* (2013.01); *G01N 27/3277* (2013.01); *G01N 2333/90203* (2013.01); *G01N 2800/28* (2013.01)

(58) Field of Classification Search
CPC ...................................................... C12Q 1/32
See application file for complete search history.

(56) References Cited

U.S. PATENT DOCUMENTS

| 6,720,164 B1 * | 4/2004 | Shinozuka | C12Q 1/005 |
| | | | 205/777.5 |
| 2010/0292178 A1 | 11/2010 | Young | |
| 2011/0155576 A1 | 6/2011 | Hwang et al. | |
| 2013/0065257 A1 | 3/2013 | Wang et al. | |

FOREIGN PATENT DOCUMENTS

| WO | 2002/047680 A2 | 6/2002 |
| WO | 03/040694 A2 | 5/2003 |
| WO | 2004/021000 A1 | 3/2004 |
| WO | 2010/104595 A1 | 9/2010 |

OTHER PUBLICATIONS

Hinman et al. JBC, 1981, 256:6583-6586.*
Dixon, Biochemical Education, 1975, 3(2):31-33.*
Howell et al. Clin Chem., 1979, 25(2):269-272.*
He Yahui, et al., "A New Optimized Spectrophotometric Assay for the Measurement of Pyruvate Dehydrogenase's Activity", Laboratory of Environmental Science, 2007, pp. 418-421.
Pushpa Sharma, et al., "Role of pyruvate dehydrogenase complex in traumatic brain injury and Measurement of Pyruvate dehydrogenase enzyme by dipstick test" J Emerg Trauma Shocll, May-Aug. 2009, 2(2): pp. 67-72.
K. Warriner, et al., "A lactate dehydrogenase amperometric pyruvate electrode exploiting direct detection of NAO+ at a poly(3-methylthiophene) :poly(phenol red) modified platinum surface", Materials Science and Engineering C 5 (1997), pp. 91-99.
European Search Report for Application No. 15799206.6-1408 I 3149466 PCT/US2015032609, dated Oct. 20, 2017.
Chinese Office action for Application No. 201580028310.7, dated Feb. 27, 2019.
Office action for European Application No. 15799206.6-1118, dated May 8, 2018.
Chinese Office action for Application No. 201580028310.7, dated Jun. 28, 2018.
Puneet et al., "Identification of S-nitroso-CoA reductases that regulate protein S-nitrosylation", Proceedings of the National Academy of Sciences, vol. 111, No. 52, Dec. 15, 2014 (Dec. 15, 2014).
Puneet et al., "Purification and Characterization of Novel Denitrosylases from Yeast and Mammals", Dec. 31, 2012 (Dec. 31, 2012), Abstract.
Shen, et al., "An iridium nanoparticles dispersed carbon based thick film electrochemical biosensor and its application for a single use, disposable glucose biosensor", Sensors and Actuators B, vol. 125 (2007) pp. 106-113.

* cited by examiner

*Primary Examiner* — Bin Shen
(74) *Attorney, Agent, or Firm* — Tarolli, Sundheim, Covell & Tummino LLP

(57) ABSTRACT

A detection system for determining pyruvate dehydrogenase (PDH) levels in a bodily sample includes at least one reaction solution for generating $NAD^+$ upon combination with PDH in the bodily sample, the reaction solution including pyruvate and NADH and a biosensor for determining the level of generated $NAD^+$.

6 Claims, 3 Drawing Sheets

SYSTEM AND METHOD FOR DETECTING NEURAL INJURY

RELATED APPLICATION

This application claims priority from U.S. Provisional Application No. 62/003,221, filed May 27, 2014, the subject matter of which is incorporated herein by reference in its entirety.

BACKGROUND

Traumatic brain injury (TBI) and related head concussion are a health issue of the civilian population due to car accidents, of people participating in contact sports, such as football, soccer, and hockey as well as a major health concern associated with the United States military. 1.7 million people suffer from TBIs annually in the United States alone. The cost of dealing with head injury, including the athletes involved in football, is both economically and emotionally expensive. TBI is the leading cause of death and disability in children and young adults. In the U.S., nearly 1-2% of the population lives with a degree of TBI-related disability.

Currently, the diagnosis of TBI-related symptoms is generally accomplished by neurological examinations and neuro-imaging tests, such as magnetic resonance imaging (MRI) and computerized tomography (CT) scanning. These tests are expensive, time-consuming, and require highly sophisticated equipment and skillful operators. Furthermore, the results are not available in a real time fashion, and the testing results are often inconclusive. Furthermore, non-contrasted CT scan may be insensitive to mild injury and can be obscured by extra-cranial injuries or the necessity for sedation and airway protection. Timely management decisions are critical in optimizing outcomes of TBI. Consequently, the value of real time diagnostic assessment given by point-of care testing of TBI is desirable to expedite appropriate treatment.

SUMMARY

Embodiments described herein relate to a detection system and in vitro assay for detecting, identifying, quantifying, and/or determining in a bodily sample the biomarkers of neural injuries, such as traumatic brain injury, as well as to a detection system and in vitro assay for diagnosing, identifying, staging, and/or monitoring neural injuries, such as traumatic brain injury, in a subject having or suspected of having a neural injury and/or neuronal disorder, such as traumatic brain injury.

In some embodiments, the detection system includes at least one reaction solution for generating nicotinamide adenine dinucleotide ($NAD^+$) upon combination with pyruvate dehydrogenase (PDH) in a bodily sample and a biosensor for determining the level of the generated $NAD^+$. In some embodiments, the at least one reaction solution can include pyruvate and NADH in quantities effective to provide substrates for reaction with PDH and the formation of lactate and $NAD^+$.

In some embodiments, the bodily sample can include a bodily fluid, such as saliva, blood, plasma, sera, breath, or urine, which can potentially include PDH.

In other embodiments, the biosensor can include a substrate, a working electrode formed on a surface of the substrate, a counter electrode formed on the surface of the substrate and a dielectric layer, which covers a portion of the working electrode and counter electrode and defines an aperture exposing other portions of the working electrode and counter electrode.

In still other embodiments, the working electrode and the counter electrode can include metalized films. For example, the working electrode and counter electrode can independently comprise gold, platinum, palladium, silver, carbon, alloys thereof, and composites thereof. The metalized films can be provided on the surface of the substrate by sputtering or coating the films on the surface and then laser ablating the films to form the working electrode and counter electrode.

In other embodiments, the sensor can include a reference electrode on the surface of the substrate. The dielectric can cover a portion of the reference electrode. The sensor can also include a measuring device for applying voltage potentials to the working electrode and counter electrode and measuring the current flow between the working electrode and counter electrode to determine the level of $NAD^+$ in a sample, such as a bodily sample.

In still other embodiments, the detection system can include other biosensors that are used to detect other biomarkers, besides PDH, which are indicative of neural injury, such as traumatic brain injury, in bodily samples from the subject. These other biomarkers can include, for example, S100B, neuron-specific enolase (NSE), and sectretagogin (e.g., SCGN, SEGN, CALBL, or setgin). The biosensors can include a substrate, a working electrode formed on a surface of the substrate, a counter electrode formed on the surface of the substrate, and a dielectric layer covering a portion of the working electrode and counter electrode and defining an aperture exposing other portions of the working electrode and counter electrode. The working electrode can be functionalized or chemically functionalized to include a receptor(s) for at least one of the biomarkers of interest. The receptor can bind selectively to one or more of the biomarkers of interest in the bodily sample.

The detection system can also include a measuring device for applying a voltage potential to the working electrode, counter electrode, and/or reference electrode and measuring the current flow between the working electrode and counter electrode. The interaction of the biomarker and the receptor, e.g., the bound biomarker, can be detected using electrochemical analytical techniques, such as cyclic voltammetry (CV), differential pulse voltammetry (DPV), to determine the presence of the biomarker in the bodily sample and whether the subject has a neural injury or the extent of the neural injury of the subject.

DETAILED DESCRIPTION

Figure 1:
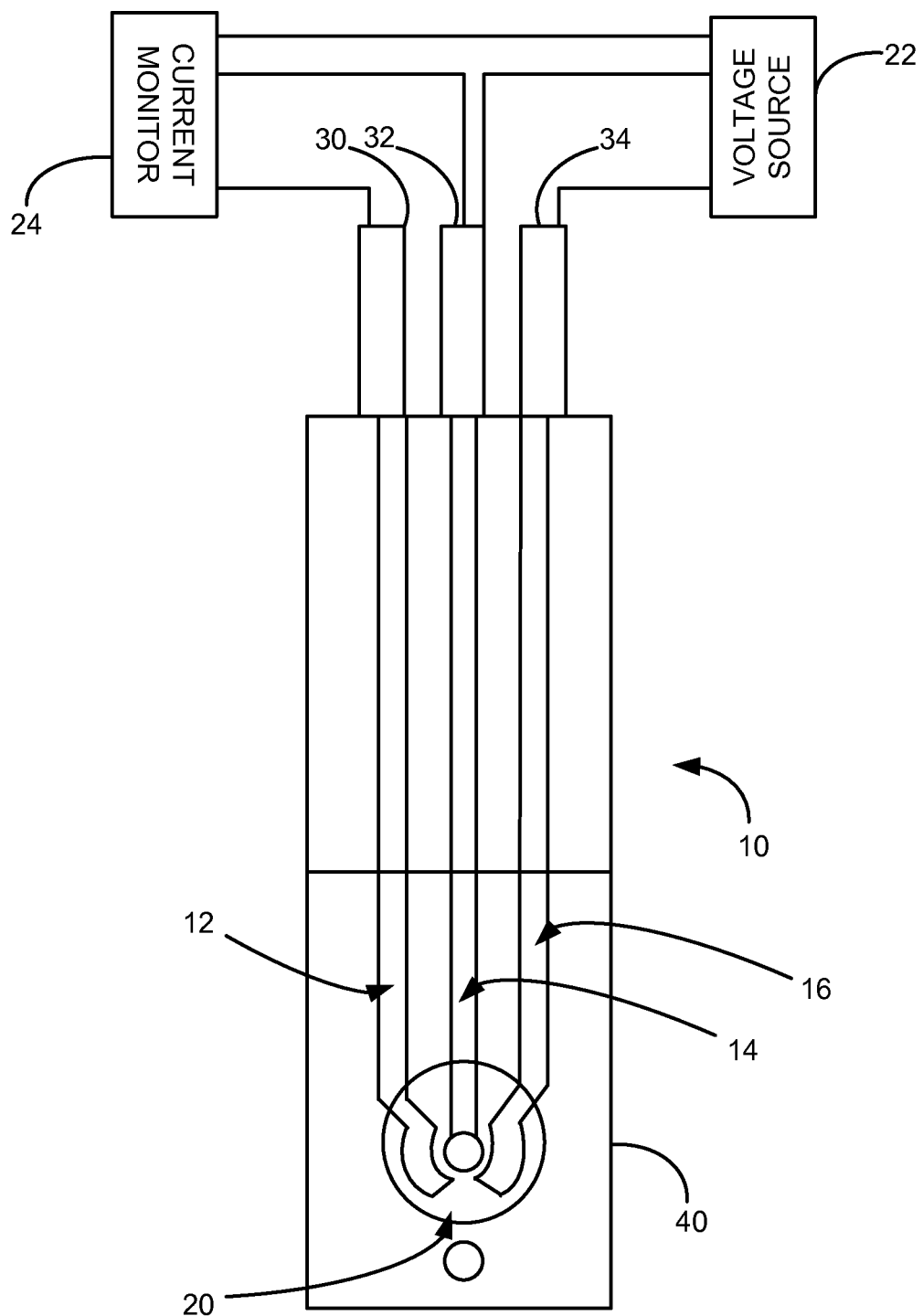
FIG. 1 is a schematic illustration of a biosensor in accordance with an aspect of the application.

Unless specifically addressed herein, all terms used have the same meaning as would be understood by those of skilled in the art of the subject matter of the application. The following definitions will provide clarity with respect to the terms used in the specification and claims.

As used herein, the term "monitoring" refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

As used herein, the term "quantitative data" or "quantitative level" or "quantitative amount" refers to data, levels, or amounts associated with any dataset components (e.g., markers, clinical indicia,) that can be assigned a numerical value.

As used herein, the term "subject" refers to a human or another mammal, which can be afflicted with a neural injury, such as a traumatic brain injury, but may or may not have such an injury. Typically, the terms "subject" and "patient" are used herein interchangeably in reference to a human individual.

As used herein, the term "injury or neural injury" is intended to include a damage which directly or indirectly affects the normal functioning of the central nervous system (CNS). For example, the injury can be damage to retinal ganglion cells; a traumatic brain injury (TBI); a stroke related injury; a cerebral aneurysm related injury; a spinal cord injury, including monoplegia, diplegia, paraplegia, hemiplegia and quadriplegia; a neuroproliferative disorder or neuropathic pain syndrome. Examples of CNS injuries or disease include TBI, stroke, concussion (including post-concussion syndrome), cerebral ischemia, neurodegenerative diseases of the brain such as Parkinson's disease, Dementia Pugilistica, Huntington's disease and Alzheimer's disease, Creutzfeldt-Jakob disease, brain injuries secondary to seizures which are induced by radiation, exposure to ionizing or iron plasma, nerve agents, cyanide, toxic concentrations of oxygen, neurotoxicity due to CNS malaria or treatment with anti-malaria agents, trypanosomes, malarial pathogens, and other CNS traumas.

As used herein, the term "stroke" is art recognized and is intended to include sudden diminution or loss of consciousness, sensation, and voluntary motion caused by rapture or obstruction (e.g., by a blood clot) of an artery of the brain.

As used herein, the term "traumatic brain injury" is art recognized and is intended to include the condition in which, a traumatic blow to the head causes damage to the brain, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF).

As used herein, the term "subject suspected of having neural injury" refers to a subject that presents one or more symptoms indicative of neural injury, such as TBI, or that is being screened for neural injury, such as TBI. A subject suspected of having neural injury, such as TBI, may also have one or more risk factors. The term encompasses individuals who have not been tested for neural injury, such as TBI, and individuals who have received an initial diagnosis but for whom the extent of the neural injury is not known.

As used herein, the term "providing a prognosis" refers to providing information regarding the impact of the presence of or extent of neural injury, such as TBI, (e.g., as determined by the methods described herein).

As used herein, the term "bodily sample" refers to a sample that may be obtained from a subject (e.g., a human) or from components (e.g., tissues) of a subject. The sample may be of any biological tissue or fluid with which biomarkers described herein may be assayed. Frequently, the sample will be a "clinical sample", i.e., a sample derived from a patient. Such samples include, but are not limited to, bodily fluids, e.g., saliva, breath, urine, blood, plasma, or sera; and archival samples with known diagnosis, treatment and/or outcome history. The term biological sample also encompasses any material derived by processing the bodily sample. Processing of the bodily sample may involve one or more of, filtration, distillation, extraction, concentration, inactivation of interfering components, addition of reagents, and the like.

As used herein, the terms "normal" and "healthy" are used interchangeably. They refer to an individual or group of individuals who have not shown any symptoms of neural injuries, and have not been diagnosed with neural injuries. Preferably, the normal individual (or group of individuals) is not on medication affecting neural injuries. In certain embodiments, normal individuals have similar sex, age, body mass index as compared with the individual from which the sample to be tested was obtained. The term "normal" is also used herein to qualify a sample isolated from a healthy individual.

As used herein, the terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal, and/or one or more individuals diagnosed with a neural injury.

As used herein, the term "indicative of neural injury", when applied to an amount of at least one PDH in a bodily sample, refers to a level or an amount, which is diagnostic of neural injury such that the level or amount is found significantly more often in subjects with the injury than in subjects without the injury (as determined using routine statistical methods setting confidence levels at a minimum of 95%). Preferably, a level or amount, which is indicative of a neural injury, is found in at least about 60% of subjects who have the neural injury and is found in less than about 10% of subjects who do not have the neural injury. More preferably, a level or amount, which is indicative of neural injury, is found in at least about 70%, at least about 75%, at least about 80%, at least about 85%, at least about 90%, at least about 95% or more in subjects who have the neural injury and is found in less than about 10%, less than about 8%, less than about 5%, less than about 2.5%, or less than about 1% of subjects who do not have the neural injury.

Embodiments described herein relate to a detection system and in vitro assay for detecting, identifying, quantifying, and/or determining in a bodily sample biomarkers of neural injuries, such as traumatic brain injury, as well as to a detection system and in vitro assay for diagnosing, identifying, staging, and/or monitoring neural injuries, such as traumatic brain injury, in a subject having, suspected of having a neural injury, such as traumatic brain injury.

The detection systems and methods described herein provide a single use, disposable, and cost-effective means for simple point-of-care, real time assessment of neural injuries, such as TBI, using bodily samples, such as bodily fluids, obtained by non-invasive or minimally invasive means, which minimizes complicated clinical procedures for detecting and monitoring TBI and related brain concussion. Detection of the chemical biomarkers of TBI has been attempted using a dipstick based immunoassay test. Unfortunately, this test still required expensive and non-portable spectrophotometric equipment. Also, the assessment is more qualitative than quantitative and inconclusive.

In some embodiments, the detection systems and assays or methods described herein include at least one reaction solution that can be used to generate a detectable and/or quantifiable analyte, which is indicative of the amount, concentration, or level of pyruvate dehydrogenase in a bodily sample of a subject suspected of having a neural injury, and a biosensor for detecting the amount, level, or concentration of the analyte in the reaction solution.

The detection of pyruvate dehydrogenase (PDH) can employ the following reaction mechanism:

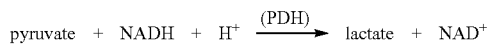

In the above reaction, pyruvate and NADH are provided in a reaction solution at quantities effective to act as substrates for reaction with PDH in a bodily sample mixed with the reaction solution, and for the production of $NAD^+$. NAD+ is an electro-chemically active species, which can be reduced at a given Gibbs free energy, or in turn, an electrochemical potential. The reduction current can be used to quantify the PDH involved in the reaction at a fixed pyruvate and NADH concentration. The amount, concentration, or level of $NAD^+$ generated by biochemical reaction of the reaction solution and PDH in the bodily sample obtained from the subject suspected of having a neural injury can be measured using a biosensor to determine the amount, concentration, or level of PDH in the bodily fluid and hence whether the subject has a neural injury.

The quantity of PDH in the bodily sample obtained from a subject suspected of having neural injury can directly affect the production of $NAD^+$. Thus, the quantified level of $NAD^+$ generated can be compared to a control or predetermined value to determine the level of PDH in the bodily sample, and if or whether the subject has a neural injury, such as TBI. For example, an increase in the detected level of $NAD^+$ in a bodily sample mixed with the reaction solution compared to a control value is indicative of the subject having a neural injury, such as TBI.

The reaction solution can be prepared, for example, by mixing quantities of pyruvate and NADH with phosphate buffered saline solution (PBS), so that the molar ratio between pyruvate and NADH is about 1:1. PBS solution with a pH of 6.5 can be prepared by mixing monobasic and dibasic sodium phosphates with deionized water, and 200 mM of potassium chloride can be added as a supporting electrolyte to improve conductivity of the buffer. Advantageously, the reaction solution does not include any reagents or byproducts that would potentially contribute to background oxidation current of the biosensor and impair detection and quantification of the $NAD^+$ generated.

The reaction solution so formed can be mixed with a bodily sample, such as a bodily fluid (e.g., saliva, blood, sera, plasma, or urine), obtained from the subject. In some aspects, the bodily fluid can be saliva that is obtained from a subject having or suspected of having a neural injury. The amount of saliva obtained from the subject can be about 0.1 ml or more. The obtained saliva can then be added to the reaction solution. For example, the amount of saliva added to about 6 µl of the reaction solution can be about 1 µl or less.

The bodily samples can be obtained from the subject using sampling devices, such as syringes, swabs or other sampling devices, used to obtain liquid and/or solid bodily samples either invasively (i.e., directly from the subject) or non-invasively. These samples can then be stored in storage containers. The storage containers used to contain the collected sample can include a non-surface reactive material, such as polypropylene. The storage containers are generally not made from untreated glass or other sample reactive material to prevent the sample from becoming absorbed or adsorbed by surfaces of the glass container.

Collected samples stored in the container may be stored under refrigeration temperature. For longer storage times, the collected sample can be frozen to retard decomposition and facilitate storage. For example, samples obtained from the subject can be stored in a falcon tube and cooled to a temperature of about −80°.

The $NAD^+$, which is generated by mixing of the bodily sample containing PDH with the reaction solution, is an electrochemically active species that can be oxidized or reduced under appropriate conditions and detected using an $NAD^+$ biosensor to quantify the level of PDH in the bodily sample and determine whether the subject has a neural injury. In some embodiments, the biosensor can include a two or three electrode electrochemical biosensor.

FIG. 1 illustrates a biosensor 10 in accordance with an embodiment of the application. The sensor 10 is a three-electrode sensor including a counter electrode 12, a working electrode 14, and a reference electrode 16 that are formed on a surface of a substrate. A dielectric layer 40 covers a portion of the working electrode 12, counter electrode 14 and reference electrode 16. The dielectric layer 40 includes an aperture 20, which defines a detection region of the working electrode 12, counter electrode 14, and reference electrode 16 that is exposed to samples in which the levels of PDH are detected.

A voltage source 22 is connected to the working and reference electrodes 14, 16. A current measuring device 24 is connected to the working and counter electrodes 14, 12 to measure the current generated by the redox reaction of $NAD^+$ when the mixture of the reaction solution and bodily sample contacts the detection region 20 of the sensor 10.

The working electrode 14 is the site of the redox reaction of $NAD^+$, and where the charge transfer occurs. The function of the counter electrode 12 is to complete the circuit, allowing charge to flow through the sensor 10. The working electrode 14 and the counter electrode 12 are preferably formed of the same material, although this is not a requirement. Examples of materials that can be used for the working electrode 14 and counter electrode 12 include, but are not limited to, gold, platinum, palladium, silver, carbon, alloys thereof, and composites thereof.

Examples of materials that can be used to form the reference electrode 16 are silver-silver chloride and mercury-mercuric chloride (Calomel). Silver-silver chloride is preferred. The silver can be applied to a substrate in the form of a silver ink, which is commercially available, or can be made using finely dispersed metal particles, solvent, and a binder. Respective silver contact pads 30, 32, and 34 are connected with each of the electrodes 12, 14, and 16. This reference electrode can be thick film printed on the same substrate of the working and counter electrode and also can be used externally.

In some embodiments, the working and counter electrodes 14, 12 can include a layer of particles, such as micro-, meso- or nano-sized particles of active carbon or porous carbon. The active carbon nanoparticles may be combined with metallic catalyst particles that increase the rate of electrochemical oxidation-reduction reaction with $NAD^+$ and provide the detection of $NAD^+$ at a lower oxidation potential than without the presence of the catalyst particles. In terms of the practical applications, the metallic catalyst particles can shorten the reaction time and lower the applied electrochemical potential for detection of $NAD^+$ in the mixture of the reaction solution and biological sample. Lowering the applied potential often leads to the minimization of electrochemical oxidation or reduction of other species presented, resulting in a minimization of interference caused by the unwanted reaction of the confounding species. As a result, a highly specific biosensor can be obtained and produced.

The metallic catalyst particles can include nano-, meso-, or micro-scale particles of a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, for example, the metallic catalyst particles may be composed of a unary metal, unary metal oxide binary metal, or binary metal oxide, such as iridium, iridium oxide, platinum, ruthenium, platinum-ruthenium, platinum-nickel, and platinum-gold.

The voltage source can apply a voltage potential to the working electrode 14 and reference and/or counter electrode 16, 12, depending on the design of the sensor 10. The current between the working electrode 14 and counter electrode 16 can be measured with a measuring device or meter. Such current is due to the reduction occurring at the working electrode 12 of $NAD^+$ in the mixture of the reaction solution and bodily sample and provided at the detection region.

The amount or level of current measured is proportional to the level or amount of $NAD^+$ in the mixture of the reaction solution and bodily sample. In some embodiments, where the sample is a bodily sample obtained from a subject that has or is suspected of having a neural injury, once the current level generated by the reaction solution tested with the sensor is determined, the level can be compared to a predetermined value or control value to provide information for diagnosing or monitoring of the neural injury in a subject. For example, the current level can be compared to a predetermined value or control value to determine if a subject has a TBI. An increased current level compared to a predetermined value or control value can be indicative of the subject having TBI; whereas similar or decreased current level compared to a predetermined value or control value can be indicative of the absence of TBI of the subject The current level generated by the mixture of the reaction solution and bodily sample obtained from the subject can be compared to a current level of a mixture of the reaction solution and bodily sample previously obtained from the subject, such as prior to administration of a therapeutic. Accordingly, the methods described herein can be used to measure the efficacy of a therapeutic regimen for the treatment of a condition, pathology, or disorder associated with neural injury in a subject by comparing the current level obtained before and after a therapeutic regimen. Additionally, the methods described herein can be used to measure the progression of the neural injury in a subject by comparing the current level in a bodily sample obtained over a given time period, such as days, weeks, months, or years.

The current level generated by the mixture of the reaction solution and bodily sample of the subject may also be compared to a predetermined value or control value to provide information for determining the severity of neural injury in the subject. A predetermined value or control value can be based upon the current level in comparable samples obtained from a healthy or normal subject or the general population or from a select population of control subjects.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

Figure 2:
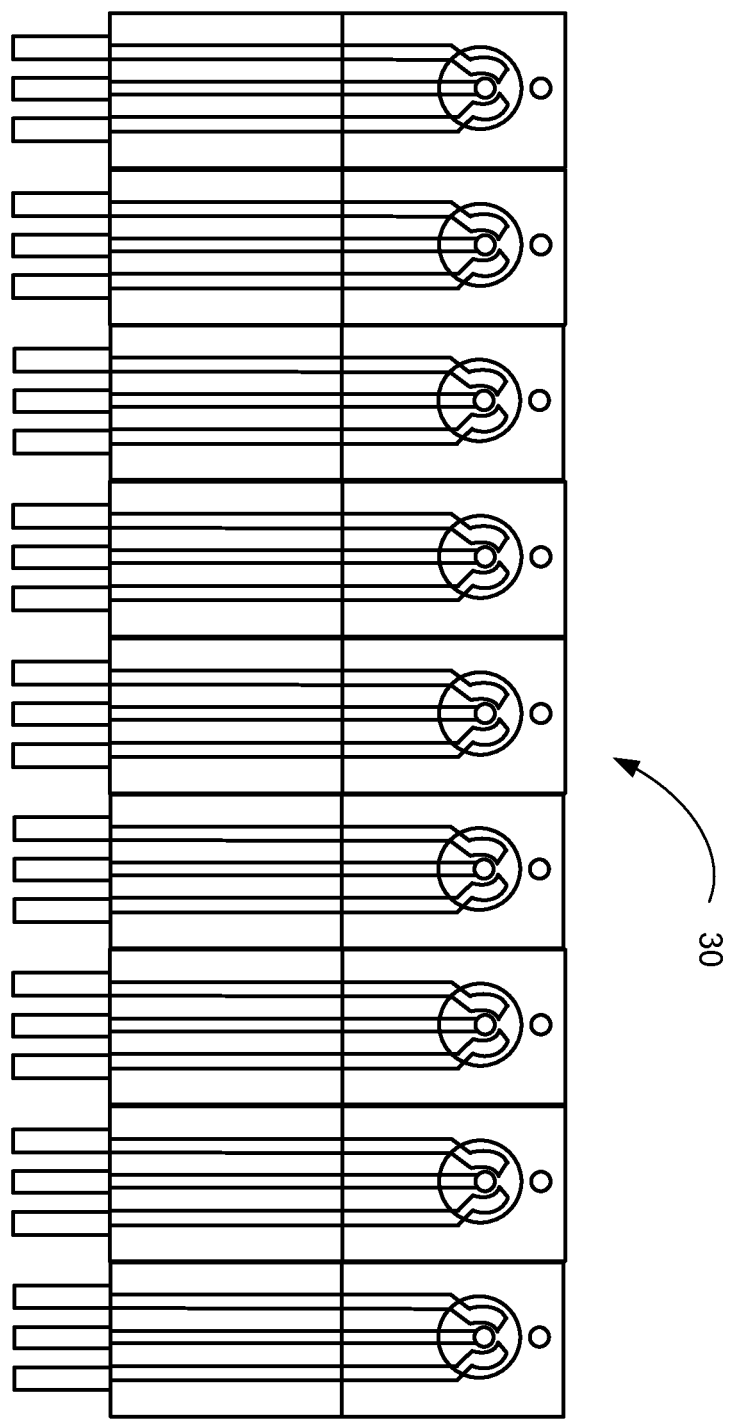
FIG. 2 is a top plan view of an array of biosensors in a row manufactured by a screen-printing process.

The biosensor illustrated in FIGS. 1 and 2 can be fabricated on a substrate 100 formed from polyester or other electrically non-conductive material, such as other polymeric materials, alumina ($Al_2O_3$), ceramic based materials, glass or a semi-conductive substrate, such as silicon, silicon oxide and other covered substrates. Multiple sensor devices 102 can thus be formed on a common substrate 100 (FIG. 2). As will be appreciated, variations in the geometry and size of the electrodes are contemplated.

The biosensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and co-pending application U.S. Ser. No. 09/466,865, which are incorporated by reference in their entirety. By way of example, in the case of the carbon electrodes, active carbon is mixed with a binder, deposited like an ink on the substrate, and allowed to dry.

In some embodiments, the working electrode, counter electrode, and reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Au, Pd, and Pt or any metal having similar electrochemical properties, that can be sputtered or coated on plastic substrates, such as PET or polycarbonate, or other dielectric material, can be irradiated using laser ablation to provide these features.

In one example, a gold film with a thickness of about 300 to about 2000 A can be deposited by a sputtering technique resulting in very uniform layer that can be laser ablated to form the working and counter electrodes. The counter electrode can use other materials. However, for the simplicity of fabrication, using identical material for both working and counter electrodes will simplify the fabrication process providing the feasibility of producing both electrodes in a single processing step. An Ag/AgCl reference electrode, the insulation layer, and the electrical connecting parts can then be printed using thick-film screen printing technique.

Figure 3:
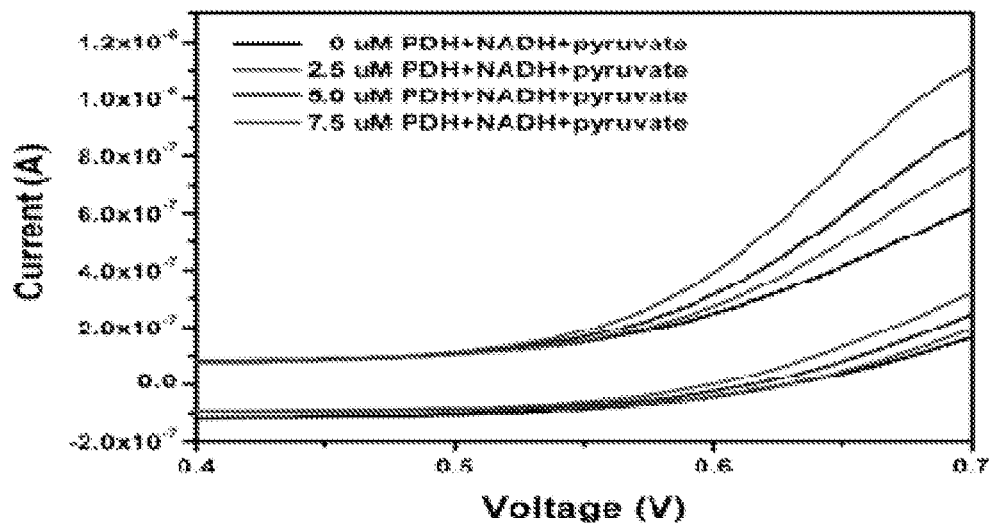
FIG. 3 illustrates plots showing cyclic voltammetric measurements of pyruvate dehydrogenase over the concentration of 0-7.5 µM. Both pyruvate and NADH are 375 µM.
Figure 4:
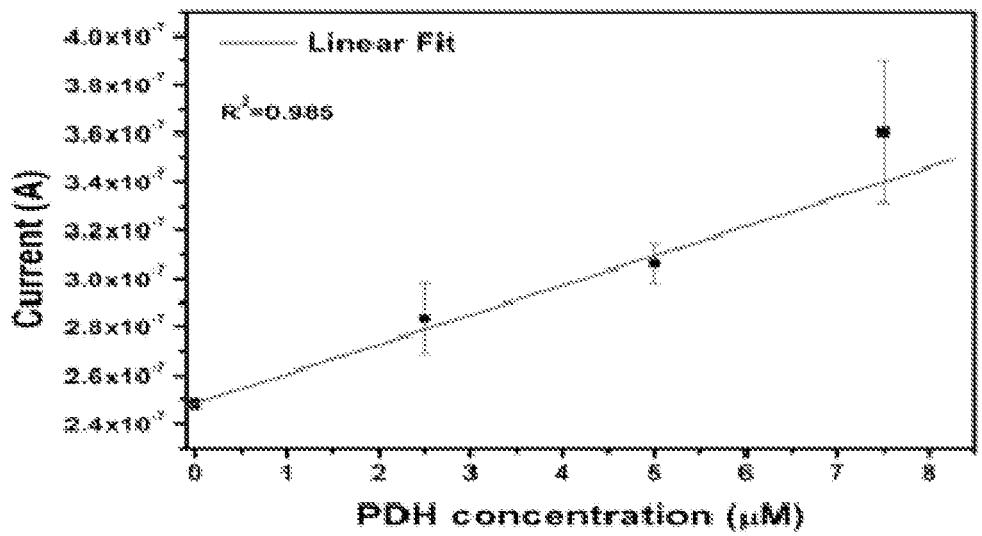
FIG. 4 illustrates a calibration curve of PDH over the concentration of 0-7.5.+0.65 V is used as the potential for the current of the cyclic voltammogram.

FIGS. 3 and 4 show that the detection system can be used to detect PDH in a solution. In preliminary testing, 3 µM of pyruvate solution (concentration of 375 µM) and 3 µl of NADH (concentration of 375 µM) were used with a PDH volume of 2 µl at a concentration varying from 0 to 7.5 µM. The results shown in FIGS. 3 and 4 employed a phosphate buffer solution (PBS). Similar to the preliminary test in PBS, initial investigation with substrate material of 3 µL of pyruvate solution (concentration 375 µM) and 3 µL of NADH (concentration 375 µM) and a PDH volume of 2 µL with a concentration varying from 0-7.5 µM performed in artificial saliva instead of PBS can be used to show saliva is a biological fluid that can be easily used to detect TBI in real time.

In other embodiments, the detection system can include other biosensors that can detect other biomarkers, besides PDH, which are indicative of neural injury, such as traumatic brain injury, in bodily samples from a subject. These other biomarkers can include, for example, S100B, neuron-specific enolase (NSE), and sectretagogin (e.g., SCGN, SEGN, CALBL, or setgin). These biosensors can include a substrate, a working electrode formed on a surface of the substrate, a counter electrode formed on the surface of the substrate, a dielectric layer covering a portion of the working electrode and counter electrode and defining an aperture exposing other portions of the working electrode and counter electrode. The working electrode can be functionalized or chemically functionalized to include a receptor(s) for at least one of the biomarkers of interest. The receptor can bind selectively to one or more of the biomarkers of interest, which are indicative of neural injury, in the bodily sample from the subject.

The detection system can also include a measuring device for applying a voltage potential to the working electrode, counter electrode, and/or reference electrode and measuring the current flow between the working electrode and counter electrode. The interaction of the biomarker and the receptor can be detected using electrochemical analytical techniques, such as cyclic voltammetry (CV), differential pulse voltammetry (DPV), to determine the presence of the biomarker in the bodily sample and whether the subject has a neural injury or the extent of the neural injury of the subject.

In some embodiments, a receptor that binds selectively to a biomarker, which is indicative of neural injury, is a molecule that binds preferentially to that biomarker (i.e., its binding affinity for that biomarker is greater than its binding affinity for any other biomarker). Its binding affinity for the biomarker of interest may be 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 100-fold or more than its binding affinity for any other biomarker. In addition to its relative binding affinity, the receptor must also have an absolute binding affinity that is sufficiently high to efficiently bind the biomarker of interest (i.e., it must have a sufficient sensitivity). Receptors having binding affinities in the picomolar to micromolar range are suitable. Such interaction can be reversible.

The receptor may be of any nature (e.g., chemical, nucleic acid, peptide, lipid, combinations thereof and the like). The biomarker, which is indicative of neural injury, too may be of any nature provided there exists a receptor that binds to it selectively and in some instances specifically.

The term "functionalized" or "chemically functionalized," as used herein, means addition of functional groups onto the surface of a material by chemical reaction(s). As will be readily appreciated by a person skilled in the art, functionalization can be employed for surface modification of materials in order to achieve desired surface properties, such as biocompatibility, wettability, and so on. Similarly, the term "biofunctionalization," "biofunctionalized," or the like, as used herein, means modification of the surface of a material so that it has desired biological function, which will he readily appreciated by a person of skill in the related art, such as bioengineering.

The receptors may be functionalized to the working electrode covalently or non-covalently. Covalent attachment of a receptor to working electrode may be direct or indirect (e.g., through a linker). Receptors may be immobilized on the working electrode using a linker. The linker can be a linker that can be used to link a variety of entities.

In some embodiments, the linker may be a homo-bifunctional linker or a hetero-bifunctional linker, depending upon the nature of the molecules to be conjugated. Homo-bifunctional linkers have two identical reactive groups. Heterobifunctional linkers are have two different reactive groups. Various types of commercially available linkers are reactive with one or more of the following groups: primary amines, secondary amines, sulphydryls, carboxyls, carbonyls and carbohydrates. Examples of amine-specific linkers are bis (sulfosuccinimidyl) suberate, bis[2-(succinimidooxycarbonyloxy)ethyl]sulfone, disuccinimidyl suberate, disuccinimidyl tartarate, dimethyl adipimate 2HCl, dimethyl pimelimidate 2HCl, dimethyl suberimidate HCl, ethylene glycolbis-[succinimidyl-[succinate]], dithiolbis(succinimidyl propionate), and 3,3'-dithiobis(sulfosuccinimidylpropionate). Linkers reactive with sulfhydryl groups include bismaleimidohexane, 1,4-di-[3'-(2'-pyridyldithio)-propionamido)]butane, 1-[p-azidosalicylamido]-4-[iodoacetamido] butane, and N-[4-(p-azidosalicylamido)butyl]-3'-[2'-pyridyldithio]propionamide. Linkers preferentially reactive with carbohydrates include azidobenzoyl hydrazine. Linkers preferentially reactive with carboxyl groups include 4-[p-azidosalicylamido]butylamine.

Heterobifunctional linkers that react with amines and sulfhydryls include N-succinimidyl-3-[2-pyridyldithio]propionate, succinimidyl[4-iodoacetyl]aminobenzoate, succinimidyl 4-[N-maleimidomethylcyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxylhydrazide HCl, 4-(4-N-maleimidophenyl)-butyric acid hydrazide.2HCl, and 3-[2-pyridyldithio]propionyl hydrazide.

Alternatively, receptors may be non-covalently coated onto the working electrode. Non-covalent deposition of the receptor to the working electrode may involve the use of a polymer matrix. The polymer may be naturally occurring or non-naturally occurring and may be of any type including but not limited to nucleic acid (e.g., DNA, RNA, PNA, LNA, and the like, or mimics, derivatives, or combinations thereof), amino acid (e.g., peptides, proteins (native or denatured), and the like, or mimics, derivatives, or combinations thereof, lipids, polysaccharides, and functionalized block copolymers. The receptor may be adsorbed onto and/or entrapped within the polymer matrix.

Alternatively, the receptor may be covalently conjugated or crosslinked to the polymer (e.g., it may be "grafted" onto a functionalized polymer).

An example of a suitable peptide polymer is poly-lysine (e.g., poly-L-lysine). Examples of other polymers include block copolymers that comprise polyethylene glycol (PEG), polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, polyvinyl chloride, polystyrene, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), poly(lactide-glycolide), copolyoxalates, polycaprolactones, polyesteramides, polyorthoesters, polyhydroxybutyric acid, polyanhydrides, poly(styrene-b-isobutylene-b-styrene) (SIBS) block copolymer, ethylene vinyl acetate, poly(meth)acrylic acid, polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, albumin and other hydrophilic proteins, zein and other prolamines and hydrophobic proteins, copolymers and mixtures thereof, and chemical derivatives thereof including substitutions and/or additions of chemical groups, for example, alkyl, alkylene, hydroxylations, oxidations, and other modifications routinely made by those skilled in the art.

In one particular embodiment, the working electrode can comprise working electrdode that is crosslinked or biotinylated chemically in order to allow attachment of an antibody or biotin containing molecule. The gold working electrode can be cross-linked for example with dithiolbis (succinimidyl propionate) (DSP), which contains amine reactive N-hydroxysuccinimide (NHS) ester that can react with amine groups of proteins and antibodies.

It will be appreciated, the flexibility of the chemical functionalization makes the biosensor useful for attaching essentially any ligand having an affinity for a biomarker. Examples of biomarkers for which ligands having affinity therefore may be attached to the working electrode include, but are not limited to DNA, oligo-nucleotides, proteins, biotin, and streptavidin. Protein ligands include monoclonal antibodies (mABs); however enzyme substrates may also be used as ligands having affinity for a corresponding enzyme.

In some embodiments, the working electrode is functionalized with monoclonal antibodies or antigen binding fragments thereof by means of a reactive amino group on the mAB. Because most antibodies have lysine groups, they can be attached to the device at the lysine amino group.

The chemical functionalization method also enables the bioconjugation of DNA aptamers having an amino group. These aptamers could potentionally bind small molecules and proteins. Once bound, the change in the charge on the surface of the working electrode would enable the device to detect the target biomolecule or small molecule.

Similar to the biosensor shown in FIG. 1 for the detection of PDH, the biosensors for the detection of other biomarkers, besides PDH, which are indicative of neural injury can be made using a thin film, thick film, and/or ink-jet printing technique, especially for the deposition of multiple electrodes on a substrate. The thin film process can include physical or chemical vapor deposition.

In some embodiments, the working electrode, counter electrode, and reference electrode of these sensors may be formed using laser ablation, a process which can produce elements with features that are less than one-thousandth of an inch. Metalized films, such as Au, Pd, and Pt or any metal having similar electrochemical properties, that can be sputtered or coated on plastic substrates, such as PET or polycarbonate, or other dielectric material, can be irradiated using laser ablation to provide these features.

In other embodiments, the detection system can include a plurality of biosensors that can be provided in an array on a surface of a substrate. The biosensor array can be configured to detect NAD+ concentration changes as well as the concentrations of other analytes indicative neural injury in a bodily sample of a subject. The biosensor array can include a plurality biosensors arranged in a plurality of rows and a plurality of columns. Each biosensor comprises on a working electrode and a counter electrode. The working electrode can be functionalized or chemically functionalized to include a receptor(s) for at least one of the analytes of interest. The receptors can be the same or different for each biosensor of the array and can bind selectively to one or more of the analytes of interest. The biosensors of the array can be configured to provide at least one output signal representing the presence and/or concentration of an analyte in the bodily sample. For each column of the plurality of columns or for each row of the plurality of rows, the array further comprises column or row circuitry configured to provide voltage potentials to respective biosensors in the column or row. Each biosensor in the row or column can potentially detect a different analyte and/or biased to detect different analytes.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A method for detecting neural injury in a subject comprising:

providing at least one reaction solution for generating NAD+ upon combination with pyruvate dehydrogenase PDH in a bodily sample obtained from the subject, the reaction solution including pyruvate and NADH; and a biosensor for determining the level of generated NAD+, wherein the biosensor including a working electrode formed on a surface of a substrate, a counter electrode formed on the surface of the substrate, and a measuring device for applying voltage potentials to the working electrode and counter electrode;

combining a bodily sample from the subject with reaction solution; and detecting the level of generated NAD+ with the biosensor by measuring the current flow between the working electrode and counter electrode, wherein an increase in the detected level of NAD+ compared to a control value is indicative of the subject having a neural injury.

2. The method of claim 1, the bodily sample comprising a bodily fluid selected from the group consisting of saliva, breath, blood, plasma, sera, and urine.

3. The method of claim 1, the neural injury comprising traumatic brain injury.

4. The method of claim 1, wherein the working electrode and the counter electrode comprise metalized films.

5. The method of claim 1, wherein the working electrode and counter electrode independently comprise gold, platinum, palladium, silver, carbon, alloys thereof, and composites thereof.

6. The method of claim 4, the metalized films are provided on the surface of the substrate by sputtering or coating the films on the surface and wherein the working electrode and the counter electrode are formed using laser ablation.

* * * * *